United States Patent [19]
Delhomme et al.

[11] Patent Number: 5,472,457
[45] Date of Patent: Dec. 5, 1995

[54] GASOLINE ADDITIVES CONTAINING ALKOXYLATED IMIDAZO-OXAZOLES

[75] Inventors: Henri Delhomme, Ste Foy les Lyons; Jean Gaillard, Saint Martin d'Heres; Philippe Mulard, St Pierre de Chandieu, France; Daniele Eber, Lyon, all of France

[73] Assignees: Institut Francais du Petrole, Rueil Malmaison; Elf Antar France, Paris LaDefense, both of France

[21] Appl. No.: 252,993

[22] Filed: Jun. 2, 1994

[30] Foreign Application Priority Data

Jun. 2, 1993 [FR] France .................... 93 06688

[51] Int. Cl.$^6$ .................... C10L 1/22; C07D 235/00
[52] U.S. Cl. .................... 44/342; 44/329; 44/341; 44/459; 548/302.7; 548/303.1
[58] Field of Search .................... 44/341, 342, 329, 44/459; 548/302.7, 303.1, 311.1

[56] References Cited

U.S. PATENT DOCUMENTS

| | | | |
|---|---|---|---|
| 2,987,515 | 6/1961 | Stromberg et al. | 260/256.4 |
| 3,251,664 | 5/1966 | Dickson et al. | 44/66 |
| 3,267,082 | 8/1966 | de Benneville et al. | 44/342 |
| 3,416,900 | 12/1968 | Dorer, Jr. | 49/342 |
| 3,560,520 | 2/1971 | Perilstein | 260/309.6 |
| 3,927,995 | 12/1975 | Romans | 44/342 |
| 4,375,974 | 3/1983 | Maldonado et al. | 44/63 |
| 4,447,611 | 5/1984 | Klaubert et al. | 548/303.1 |
| 4,477,261 | 10/1984 | Sung | 44/342 |
| 4,968,321 | 11/1990 | Sung et al. | 44/459 |

FOREIGN PATENT DOCUMENTS

| | | |
|---|---|---|
| 0180910 | 5/1986 | European Pat. Off. . |
| 0444770 | 9/1991 | European Pat. Off. . |
| 494770 | 7/1967 | Germany . |
| 57-094069 | 6/1982 | Japan . |

OTHER PUBLICATIONS

Patent Abstracts of Japan, vol. 6, No. 177 (C–124) Jun. 11, 1982.
Chemical Abstracts, vol. 77, No. 4, Abstract No. 20861z, Jul. 24, 1972.
Chemical Abstracts vol. 93, No. 26, Abstract No. 240687t, Dec. 29, 1980.
Sano et al., "Zwitterions of 1–Poly(oxyethylene)–2–imidazoline Derivatives as Anti–Electrostatic Agent for Polyamide Fiber", *Polymer Bulletin*, vol. 6, 343–349 (1982), (Month N/A).

*Primary Examiner*—Ellen M. McAvoy
*Attorney, Agent, or Firm*—Millen, White, Zelano & Branigan

[57] ABSTRACT

Compounds with general formula

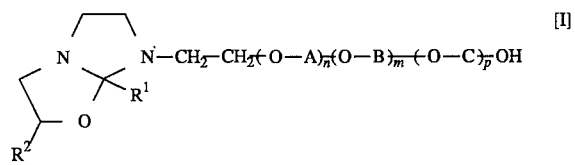

where $R^1$ represents a hydrogen atom or a hydrocarbon group containing 1 to 40 carbon atoms. $R^2$ represents a hydrogen atom or a hydrocarbon group containing 1 to 12 carbon atoms, A, B, and C, which may be identical or different, each represent a divalent hydrocarbon group containing 2 to 6 carbon atoms, n is a whole number from 5 to 50, m and p are each zero or a whole number from 1 to 25, and the sum n+m+p is a whole number from 5 to 50.

These compounds are used in multifunctional additive compositions for fuels used in internal combustion engines, in particular spark ignition engines, in admixture with at least one compound selected from the group formed by detergent-dispersant compounds, and at least one compound selected from the group formed by mineral or synthetic lubricating oils and polyglycols which are soluble in said fuels.

24 Claims, No Drawings

GASOLINE ADDITIVES CONTAINING ALKOXYLATED IMIDAZO-OXAZOLES

BACKGROUND OF THE INVENTION

The present invention relates to additive formulations, particularly for fuels, comprising at least one alkoxylated imidazo-oxazole compound, at least one compound selected from the group formed by detergent-dispersant products and at least one product selected from the group formed by mineral or synthetic lubricating oils and polyglycols which are soluble in said fuel. These formulations may be used as multifunctional additives for fuels used in internal combustion engines, in particular spark ignition engines.

Use of conventional fuels often results in coking of engine parts due to incomplete vaporisation and combustion of the fuel in the intake system and combustion chambers.

When using spark ignition engines in particular, the formation and accumulation of deposits in the combustion chambers adversely affects the normal operating conditions of the engine.

These deposits significantly affect thermal exchange between the combustion chambers and the engine cooling system by forming an insulating layer.

This results in an increase in the temperature in the chambers to which the gas mixture is submitted. This encourages self-ignition of these gases, and the well known phenomenon of pinging then occurs.

In addition, accumulation of deposits in the combustion chambers can reduce the volume of the combustion zone leading to an increase in the compression ratio of the engine. This can also encourage pinging. Further, the deposits formed in the various engine parts which come into contact with the fuel can partially absorb a portion of the fuel and thus change the oxidant-fuel mixture resulting in a fuel depleted phase during absorption and an enriched phase during fuel desorption. If the fuel-air mixture is altered, the engine can no longer operate under optimal conditions.

Coking can be removed by periodic cleaning of the elements affected, in particular the valves. This is particularly onerous.

Accumulation of deposits in the engines, in particular on the intake valves, can also be reduced by employing fuels containing certain additives, for example detergent type additives which may be combined with anticorrosive or antideposit additives for the combustion chamber, for example.

Additives are well known industrially, for example polyisobutene-amine type additives, normally associated with a mineral or synthetic oil. They can lead to increased coking in the combustion chambers and thus an increase in the octane requirement of the engine with a greater sensitivity to pinging.

Examples of prior art additives are the condensation products of polyalkenylsuccinic anhydrides with polyamines such as, tetraethylenepentamine, which are particularly described in U.S. Pat. No. 3,172,892. These additives exhibit good anticorrosive properties but are not effective as valve detergents.

Condensation products of polyalkenylsuccinic anhydrides with hydroxyimidazolines, in particular 1-(2-hydroxyethyl)imidazolines substituted in the 2 position by an alkyl or alkenyl group, may also be cited. These are described, for example, in European patent application EP-A-74 724. The products described in this application are good engine fuel additives and exhibit good anticorrosive properties, but are not very carburettor cleaners.

Coking of the combustion chambers occurs progressively during engine operation. This is characterised by its octane requirement which corresponds to the minimum octane number of the fuel required in the engine for it to operate without pinging. When the octane requirement exceeds the octane number of the fuel supplied to the engine, particularly when the combustion chambers are coked, pinging occurs. The increase in the octane requirement of the engine is known to the skilled person as ORI or "Octane Requirement increase".

The onset of pinging and its onerous consequences such as fatigue and increased wear of essential parts can be limited by avoiding too high an octane requirement by using a higher octane fuel than previously used, provided this is available and the higher costs can be tolerated. The combustion chambers can also be cleaned periodically to eliminate the deposits formed and reduce the engine octane requirement. This operation is, however, long and expensive.

Many patent documents describe additives for particular use in engine fuels. Compositions such as those described in European patent EP-A-327 097, for example, exhibit good anti-ORI properties but have relatively limited detergent properties. In addition, these compositions are not described as exhibiting good anticorrosive properties.

SUMMARY OF THE INVENTION

We have now surprisingly discovered, as will be described below, formulations which may in particular be used as multifunctional additives for engine fuels, in particular fuels used in spark ignition engines. The formulations of the present invention have excellent detergent properties as regards the intake valves and carburettor or injectors, and also have very good anticorrosive properties.

Formulations according to the present invention can be used as multifunctional additives for fuels and, for example, as additives in fuels used in spark ignition engines in which they in particular limit the octane requirement increase (ORI) in these engines and thus limit, retard or even avoid the onset of pinging.

Formulations in accordance with the present invention associate this anti-ORI action with a detergent action in the carburettor, the injectors and in the intake valves. These formulations also exhibit anticorrosive properties both when used in spark ignition engine fuels and in those used in compression ignition engines (Diesel engines). Further, the use of these formulations in fuels employed in spark ignition engines avoids sticking in the intake valves and also does not contribute to the formation of deposits (black sludge) in the engine lubricating oils.

The object of the present invention is to provide an additive formulation, in particular for a fuel, comprising at least one constituent (K), at least one constituent (L) and at least one constituent (M), said constituent (K) consisting of at least one imidazo-oxazole type heterocyclic compound containing an alkoxylated side chain, and having general formula (I):

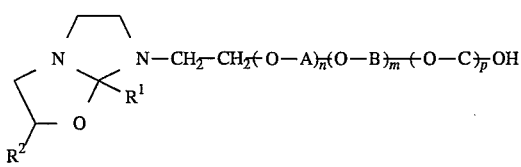

where $R^1$ represents a hydrogen atom or a hydrocarbon group containing 1 to 40 carbon atoms, preferably 4 to 25 carbon atoms, $R^2$ represents a hydrogen atom or a hydrocarbon group containing 1 to 12 carbon atoms, preferably 1 to 6 carbon atoms and more preferably 1 to 3 carbon atoms, A, B, and C, which may be identical or different, each represent a divalent hydrocarbon group containing 2 to 6 carbon atoms, preferably 2 to 4 carbon atoms, n is a whole number from 5 to 50, preferably 10 to 50 and more preferably 10 to 25, m and p, which may be identical or different, are each zero or a whole number from 1 to 25, and the sum n+m+p is a whole number from 5 to 50, preferably 10 to 50 and more preferably 10 to 25, said constituent (L) consisting of at least one compound selected from the group formed by detergent-dispersant products, and said constituent (M) consisting of at least one compound selected from the group formed by mineral or synthetic lubricating oils and polyglycols which are soluble in said fuel.

Examples of fuels which could contain at least one additive formulation in accordance with the invention are petrols such as those defined in standard ASTM D-439, and gas oils or Diesel fuels such as those defined in standard ASTM D-975. These fuels may also contain other additives, particularly in fuels for spark ignition engines, such as antiknock agents, for example lead compounds (such as tetraethyl lead), ethers such as methytertiobutylether or methyltertioamylether or a mixture of methanol and tertiobutyl alcohol and antifreeze agents. Formulations in accordance with the present invention may also be added to non hydrocarbon fuels such as alcohol or a mixture of alcohols.

Constituent (K) is more preferably selected from compounds with general formula (I) above where $R^1$ represents an alkoyl, alkenyl, aryl, alkaryl or aralkyl group, preferably a linear or branched alkoyl or alkenyl group, $R^2$ more preferably represents a hydrogen atom or a linear or branched, preferably linear, alkoyl group.

Preferred constituents (K) with formula (I) are those where m and p equal zero, A represents an alkoxylene group containing 2 to 4 carbon atoms and $R^2$ represents a hydrogen atom when A is a dimethylene group with formula —$CH_2$—$CH_2$— and an alkoyl group, preferably linear, containing 2 carbon atoms less than group A when the latter represents an alkoxylene group containing 3 or 4 carbon atoms. More preferred compounds are those where A represents a dimethylene group, a 1-methyl dimethylene group or a 1-ethyl dimethylene group, respectively derived from ethylene oxide, propylene oxide and 1-butene oxide with the following formulae:

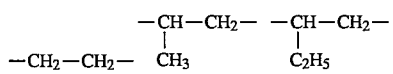

Heterocyclic imidazo-oxazole type compounds used as constituent-(K) may be manufactured using any method known to the skilled person. By way of non limiting example, the following methods may be used to prepare compounds with general formula (I) above. The method will be illustrated in a subsequent example.

According to this method, at least one alkylene oxide containing 2 to 6 carbon atoms, preferably 2 to 4 carbon atoms per molecule is reacted with at least one 1-(2-hydroxyethyl)-imidazoline which may be unsubstituted or substituted in the 2 position by a hydrocarbon group containing 1 to 40 carbon atoms and having the following general formula (II):

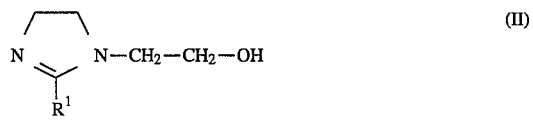

where $R^1$ is as defined above. The reaction is carried our in the presence or absence of an inert organic solvent, at a temperature of about 90° C. to about 190° C., more preferably about 100° C. to 140° C., in the presence of a basic catalyst.

The reaction is generally carried out at a pressure of about 1 to 7 bar (1 bar equals 0.1 megapascal). The reaction time varies depending on the alkylene oxide used and the number of moles of alkylene oxide used per mole of imidazoline. This reaction time is normally about 6 to about 24 hours (h), preferably about 7 to about 10 hours. The molar ratio of imidazoline to alkylene oxide is normally about 1:5 to about 1:50, preferably about 1:10 to about 1:50 and more preferably about 1:10 to about 1:25. About 0.1 to about 0.6 moles of basic catalyst per mole of imidazoline is normally used. The catalyst is eliminated at the end of the reaction either by washing with water or by ion exchange treatment, for example using a solid ion exchanger.

The basic catalyst is normally selected from the group formed by sodium methylate, sodium ethylate, potassium tertiobutylate, potash and soda.

The alkylene oxide is more preferably selected from the group formed by ethylene oxide, propylene oxide and 1-butene oxide.

The imidazolines used to prepare the imidazo-oxazole type heterocyclic compounds of the present invention are known compounds, certain of which are commercially available. Imidazolines with formula (II) are, for example, described in European patent application EP-A-74 724. These imidazolines are preferably synthesised by reaction of at least one organic carboxylic acid with N-(2-hydroxyethyl)-ethylenediamine. The reaction proceeds via a first amide formation step followed by cyclisation. The organic acids used generally contain 2 to 25 carbon atoms; they are preferably monocarboxylic aliphatic acids.

Examples of acids are acetic acid, propanoic acid, butanoic acid, caproic acid, capric acid, lauric acid, myristic acid, palmitic acid, stearic acid, behenic acid, cerotic acid and the following unsaturated fatty acids:

| | |
|---|---|
| $CH_3$—$CH_2$—CH=CH—(—$CH_2$—)$_7$—COOH | dodecylenic acid |
| $CH_3$—(—$CH_2$—)$_5$—CH=CH=(—$CH_2$—)$_7$—COOH | palmitoleic acid |
| $CH_3$—(—$CH_2$—)$_7$—CH=CH—(—$CH_2$—)$_7$—COOH | oleic acid |
| $CH_3$—(—$CH_2$—)$_5$—CHOH—$CH_2$—CH=CH— (—$CH_2$—)$_7$—COOH | ricinoleic acid |
| $CH_3$—(—$CH_2$—)$_{10}$—CH=CH—(—$CH_2$)$_4$—COOH | petroselenic acid |
| $CH_3$—(—$CH_2$—)$_5$—CH=CH—(—$CH_2$—)$_9$—COOH | vaccenic acid |
| $CH_3$—(—$CH_2$—)$_4$—CH=CH—$CH_2$—CH=CH— (—$CH_2$—)$_7$—COOH | linoleic acid |
| $CH_3$—(—$CH_2$—)$_9$—CH=CH—(—$CH_2$—)$_7$—COOH | gadoleic |

| | |
|---|---|
| $CH_3-(-CH_2-)_9-CH=CH-(-CH_2-)_9-COOH$ | acid cetoleic acid |
| $CH_3-(-CH_2-)_7-CH=CH-(-CH_2-)_{11}-COOH$ | erucic acid |
| $CH_3-(-CH_2-)_7-CH=CH=(-CH_2-)_{13}-COOH$ | selacholeic acid |

1-(2-hydroxyethyl)-2-heptadecenyl imidazoline, for example, may be used, prepared for example from oleic acid and N-(2-hydroxyethyl)-ethylenediamine. This preparation is, for example, described in U.S. Pat. No. 2,987,515. 1-(2-hydroxyethyl)-2-methyl imidazoline may also be cited as an example, prepared for example from acetic acid and N-(2-hydroxyethyl)ethylenediamine. 1-(2-hydroxyethyl)-2-heptadecenylimidzoline is sold by CIBA-GEIGY under the trade name "Amine-O".

Formulations in accordance with the present invention comprise at least one constituent (L) selected from the group formed by detergent-dispersant products. Constituent (L) is generally selected from the group formed by polyolefins, preferably polyisobutenes, polyisobutene-amines, mixtures of these compounds and products which are particularly described in our European patent application EP-A-349 369, also those described in U.S. Pat. No. 4,375,974. The products described in European patent application EP-A-349 369 are produced from the reaction in a first step of at least one succinic derivative selected from the group formed by alkenylsuccinic acids and anhydrides and polyalkenylsuccinic acids and anhydrides with at least one 1-(2-hydroxyethyl)-imidazoline substituted in the 2 position by a linear or branched alkyl or alkenyl radical containing 1 to 25 carbon atoms, the imidazoline/succinic derivative molar ratio being from. 0.1:1 to 0.9:1, preferably 0.2:1 to 0.8:1 and more preferably 0.3:1 to 0.7:1, said step being carried out under conditions such that at least 0.15 moles of water per mole of imidazoline is formed and eliminated; and in a second step of the reaction, the product from the first step is reacted with at least one polyamine with one of the following general formulae:

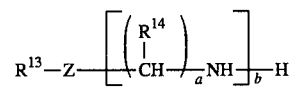  (III)

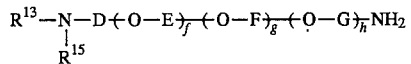  (IV)

where $R^{13}$ represents a hydrogen atom or a hydrocarbon group containing 1 to 60 carbon atoms, Z is selected from the groups —O— and —$NR^{15}$— where $R^{15}$ represents a hydrogen atom or a hydrocarbon group containing 1 to 60 carbon atoms, $R^{13}$ and $R^{15}$ being capable of forming a heterocycle with the nitrogen atom to which they are bonded, each $R^{14}$ group independently represents a hydrogen atom or a hydrocarbon group containing 1 to 4 carbon atoms, a is a whole number from 2 to 6, b is a whole number from 1 to 10 when Z represents —$NR^{15}$— and a whole number from 2 to 10 when Z is —O—, D, E, F and G, which may be identical or different, each represent a divalent hydrocarbon group containing 2 to 6 carbon atoms, f is a whole number from 1 to 60, g and h, which may be identical or different, are each zero or a whole number from 1 to 50 and the sum f+g+h is a whole number from 1 to 60, the quantity of polyamine used in the reaction being at least 0.1 mole per mole of succinic derivative introduced in the first step. The total quantity of substituted imidazoline and polyamine is preferably 0.8 to 1.2 mole per mole of succinic derivative.

The acid or acid derivative used within the context of the present invention to prepare constituent (L) is generally a succinic compound or an alkylsuccinic or alkenylsuccinic compound, preferably a succinic anhydride. Examples of succinic compounds are succinic anhydride, methylsuccinic anhydride usually known as citraconic anhydride, and alkylsuccinc or alkenylsuccinc anhydrides generally with an average molecular weight of about 200 to 3000, preferably 500 to 2000 and more preferably 700 to 1500. These succinic derivatives are widely described in the prior art: they may, for example, be obtained by the action of at least one alpha olefin or chlorinated hydrocarbon with maleic acid or anhydride. Tie alpha olefin or chlorinated hydrocarbon used for this synthesis may be linear or branched, and generally contains 10 to 150 carbon atoms, preferably 15 to 80 carbon atoms and more preferably 20 to 75 carbon atoms per molecule. The olefin may also be an oligomer, for example a dimer, trimer or tetramer, or a low olefin polymer containing, for example, 2 to 10 carbon atoms, such as ethylene, propylene, n-but-1-ene, isobutene, n-hex-1-ene, n-oct-1-ene, 2-methyl-hept-1-ene or 2-methyl-5-propyl-hex-1-ene. Mixtures of olefins or chlorinated hydrocarbons may be used.

Examples of succinic anhydrides are n-octadecenylsuccinic anhydride, dodecenylsuccinic anhydride and polyisobutenylsuccinic anhydrides, usually termed PIBSA, with an average molecular weight as defined above.

1-(2-hydroxyethyl)-imidazolines substituted in the 2 position by an alkyl or alkenyl radical containing 1 to 25 carbon atoms used in the present invention to prepare constituent (L) are generally commercially available compounds or those which can be synthesised, for example, by reaction of at least one organic acid with N-(2-hydroxyethyl)-ethylenediamine. The reaction proceeds as described above and the acids used are those mentioned above regarding the preparation of compounds with general formula (I). One of the imidazolines mentioned above may be used.

The first step in preparing constituent (L) is generally carried out by gradual addition of the imidazoline derivative to a solution of the succinic derivative in an organic solvent at room temperature, then heating to a temperature of generally between 65° C. and 250° C., preferably between 80° C. and 200° C. The organic solvent used for this preparation has a boiling point of between 65° C. and 250° C. and is generally selected to allow elimination of the water formed during the course of the condensation reaction of the imidazoline with the succinic derivative, preferably in the form of a water-organic solvent azeotrope. Examples of organic solvents which are normally used are benzene, toluene, xylenes, ethylbenzene or a hydrocarbon fraction such as the commercially available fraction SOLVESSO 150 (190°–209° C.) containing 99% by weight of aromatic compounds. Solvent mixtures may be used, for example a xylene mixture. The heating period following addition of the imidazoline is normally 0.5 to 7 hours, preferably 1 to 5 hours. This first step is preferably carried out at the selected temperature until all the water formed during the reaction has been released.

The quantity of water eliminated during the first step is normally about 0.15 to 0.6 mole, more preferably about 0.5 moles per mole of imidazoline involved in the reaction. At least one polyamine, preferably diluted in an organic solvent, is preferably gradually added to the product or mixture from the first step, if necessary following cooling, then the whole is heated to a temperature of between 65° C. and 250° C., preferably between 80° C. and 200° C. The solvent used in the second step is preferably the same as that used in the first step and the temperature is also the same during the two steps. The reactions are generally carried out at a temperature corresponding to the reflux temperature. Heating during this second step is generally carried out for 0.1 to 7 hours, preferably 0.2 to 5 hours. The quantity of polyamine used is at least 0.1 mole per mole of succinic anhydride introduced in the first step, preferably such that the total quantity of substituted imidazoline and polyamine used in the preparation is 0.8 to 1.2 mole. Preferably 0.9 to 1.1 mole per mole of succinic derivative. The substituted imidazoline: polyamine molar ratio is preferably from 1:1 to 7:1, more preferably from 1:1 to 3:1.

The quantity of water eliminated during the course of the second step is generally such that the total quantity of water eliminated during the two successive reactions is 0.2 to 0.7 moles per mole of succinic derivative.

Polyamines with formula (III) are preferably those where $R^{13}$ is a hydrogen atom or a hydrocarbon group containing 1 to 30 carbon atoms, Z is preferably a —$NR^{15}$— group where $R^{15}$ preferably represents a hydrogen atom or a hydrocarbon group containing 1 to 30 carbon atoms, preferably each $R^{14}$ group independently represents a hydrogen atom or a methyl group, a is a whole number from 2 to 4 and when Z is a —$NR^{15}$— group, b is preferably a whole number from 1 to 5.

Compounds with formula (II) above which are advantageously used are those where Z is —$NR^{15}$—, $R^{13}$, $R^{14}$ and $R^{15}$ each represent a hydrogen atom, a is equal to 2 and b is a whole number from 1 to 5, or those where $R^{13}$ represents a hydrocarbon group preferably containing 5 to 24 carbon atoms, Z represents a —$NR^{15}$— group where $R^{15}$ is a hydrogen atom, $R^{14}$ represents a hydrogen atom, a is a whole number from 2 to 4, preferably 3, and b is a whole number from 1 to 5, preferably 1.

Hydrocarbon groups $R^{13}$ and $R^{15}$ are generally linear or branched alkyl or alkenyl groups, aryl, arylalkyl (aralkyl) groups, alkylaryl (alkaryl) groups or cycloaliphatic groups. Groups $R^{13}$ and $R^{15}$ are preferably linear or branched alkyl or alkenyl groups. Hydrocarbon group $R^{14}$ is generally an alkyl group, preferably linear, for example methyl, ethyl, n-propyl or n-butyl.

The following specific compounds may be cited: the biprimary alpha-omega diamines mentioned above, trimethylenediamine, 2,2,4- and 2,4,4-trimethyl hexamethylenediamine, N-alkyl 1,3-diaminopropanes, for example N-dodecyl 1,3-diaminopropane, N-tetradecyl 1,3-diaminopropane, N-hexadecyl 1,3-diaminopropane, N-octadecyl 1,3-diaminopropane, N-eicosyl 1,3-diaminopropane and N-docosyl 1,3-diaminopropane; N-alkyldipropylene triamines, for example N-hexadecyl dipropylenediamine, N-octadecyl dipropylenediamine, N-eicosyl dipropylenediamine and N-docosyl dipropylenediamine; N-alkenyl 1,3-diaminopropanes and N-alkenyl dipropylene triamines, for example N-octadecenyl 1,3-diaminopropane, N-hexadecenyl 1,3-diaminopropane, N-dodecylenyl 1,3-diaminopropane, N-octadecadienyl 1,3-diaminopropane and N-docosenyl 1,3-diaminopropane. Examples of N,N disubstituted diamines are N,N-diethyl 1,2-diaminoethane, N,N-diisopropyl 1,2-diaminoethane, N,N-dibutyl 1,2-diaminoethane, N,N-diethyl 1,4-diaminobutane, N,N-dimethyl 1,3-diaminopropane, N,N-diethyl 1,3-diaminopropane, N,N-dioctyl 1,3-diaminopropane, N,N-didecyl 1,3-diaminopropane, N,N-didodecyl 1,3-diaminopropane, N,N-ditetradecyl 1,3-diaminopropane, N,N-dihexadecyl 1,3-diaminopropane, N,N-didodecyl 1,3-diaminopropane, N,N-didodecyl dipropylene triamine, N,N-ditetradecyl dipropylene triamine, N,N-dihexadecyl dipropylene triamine, N,N-dioctadecyl dipropylene triamine, N-methyl, N-butyl 1,2-diaminoethane, N-methyl N-octyl 1,2-diaminoethane, N-ethyl, N-octyl 1,2-diaminoethane, N-methyl N-decyl 1,2-diaminoethane, N-methyl N-dodecyl 1,3-diaminopropane, N-methyl N-hexadecyl 1,3-diaminopropane and N-ethyl N-octadecyl 1,3-diaminopropane.

Examples of etheramines are N-(3-octyloxypropyl) 1,3-diaminopropane, N-(3-decyloxypropyl) 1,3-diaminopropane and N-[(2,4,6-trimethyldecyl) 3-oxypropyl] 1,3-diaminopropane.

It should be noted that one or more compounds with formula (III) and/or (IV) can be employed. The following specific examples of mixtures of compounds with formula (III) may be cited:

fatty diamine fractions with formula $R^{13}$—NH—(—$CH_2$—)$_3$—$NH_2$ where groups $R^{13}$ are $C_8$, $C_{10}$, $C_{12}$, $C_{14}$, $C_{16}$, $C_{18}$, $C_{20}$ and $C_{22}$ aliphatic hydrocarbon radicals in the approximate molar proportions which are given in Table I below.

TABLE I

| Alkyl chains Fraction | $C_8$ % | $C_{10}$ % | $C_{12}$ % | $C_{14}$ % | $C_{16}$ % | $C_{18}$ % | $C_{18-1}$* % | $C_{20}$ % | $C_{22}$ % |
|---|---|---|---|---|---|---|---|---|---|
| H | 0 | 0 | 0 | 1 | 28 | 71 | 0 | 0 | 0 |
| I | 0 | 0 | 0 | 1 | 5 | 42 | 0 | 12 | 40 |
| J | 3 | 6 | 56 | 18 | 10 | 2 | 5 | 0 | 0 |
| N | 0 | 0 | 0 | 0 | 16 | 4.9 | 79.1 | 0 | 0 |
| P | 0 | 0 | 0 | 2.3 | 31.8 | 24.2 | 39 | 2.7 | 0 |

*$C_{18-1}$ Chain containing one unsaturated ethylene bond.

Preferred polyamines with formula (IV) are those in which $R^{13}$ and $R^{15}$ each represent a hydrogen atom, D, E, F and G, which may be identical or different, each represent an alkylene group containing 2 to 4 carbon atoms, for example ethylene, trimethylene, methylethylene, tetramethylene, methyltrimethylene, 1-methyl trimethylene and 2-methyl trimethylene, f is a whole number from 1 to 60 and g and h are equal to zero or f is a whole number from 1 to 59, h is zero or a whole number such that the sum f+h is from 1 to 59 and g is a whole number from 1 to 60, where in each case the sum f+g+h equals a whole number from 1 to 60.

Biprimary alpha-omega diamines, which are well known in the art, may be cited as specific compounds with formula (IV). The following specific compounds may be cited by way of non limiting example: ethylenediamine, propylenediamine, diethylenetriamine, dipropylenetriamine, triethylenetetramine, tripropylenetetramine, tetraethylenepentamine, tetrapropylenepentamine, hexamethylenediamine, di(trimethylene)-triamine, 2,2-dimethylpropane 1,3-diamine, N,N'-bis(3-aminopropyl)-ethylenediamine, (2'-aminoethyl)-3-amino propylamine, and trimethyl-hexamethylenediamines when the amine formula contains no oxygen atoms. When the amine formula contains oxygen atoms, polyamines with the following formula may be cited:

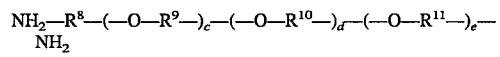

where $R^8$, $R^9$, $R^{10}$ and $R^{11}$, which may be identical or different, preferably each represent an alkylidene group containing 2 to 4 carbon atoms, for example ethylidene (dimethylene), propylidene (trimethylene), isopropylidene (1-methyl dimethylene), butylidene (tetramethylene), isobutylidene (2-methyl trimethylene), c is preferably a whole number from 1 to 60 and d and e equal zero or c is a whole number from 1 to 59, e is zero or a whole number such that the sum c+e is from 1 to 59 and d is a whole number from 1 to 50, where in each case the sum c+d+e is a whole number from 1 to 60.

Further specific diamines which may be cited are these with the following formulae (V), (VI) and (VII):

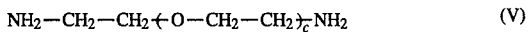

(V)

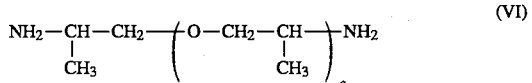

(VI)

where c is 2, 3, 5, 6 or about 33, or formula:

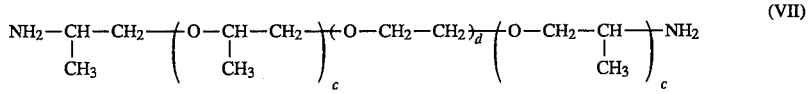

(VII)

where d is about 8, 9, 15, 16 or 40 and c+e is about 2 or 3.

These particular products are sold by TEXACO CHEMICAL under the trade name Jeffamine EDR 148 for the product with formula (V) where c=2, Jeffamine D-230 for the product with formula (VI) with an average molecular weight of 230, Jeffamine D-400 for the product with formula (VI) with an average molecular weight of 400, Jeffamine D-2000 for the product with formula (VI) with an average molecular weight of 2000, Jeffamine ED-600 for the product with formula (VII) with an average molecular weight of 600, Jeffamine ED-900 for the product with formula ( VII ) with an average molecular weight of 900 and Jeffamine ED-2001 for the product with formula (VII) with an average molecular weight of 2000. One or more biprimary diamines may be used in the present invention for product synthesis.

The products described by us in U.S. Pat. No. 4,375 974 and usable as constituent (L) in the present invention are those produced from the reaction of at least one polyamine, containing at least one primary amine group and with general formula (III) above, with at least one succinic derivative as described above, said reaction being carried out under conditions suitable for the formation and elimination of water of reaction. More preferably, the reaction is carried out at a temperature of about 120° C. to about 200° C. with an amine:succinic derivative molar ratio of about 0.9:1 to about 1.2:1. This reaction may be carried out in the absence of a solvent or in the presence of a solvent such as an aromatic hydrocarbon or a hydrocarbon fraction with a boiling point of about 70° C. to about 250° C.

Constituent (L) of the present invention may also be selected from the group formed by polyisobutenes, polyisobutene-amines, and mixtures of these compounds The polyolefins used may be polymers or copolymers or the corresponding amine or hydrogenated derivatives formed from hydrocarbons containing 2 to 10 carbon atoms per molecule.

These polymeric compounds are normally prepared from mono-olefinic or diolefinic compounds with an average molecular weight of 500 to 10000, preferably about 500 to 3500 and more preferably about 650 to 2600. More preferably, the starting compounds used in the manufacture of these polymers are olefins containing 2 to 6 carbon atoms per molecule, such as ethylene, propylene, isopropylene, butene, isobutene, amylene, hexylene, butadiene and isoprene. Most preferably, propylene, isopropylene, butene and isobutene are used. Other polyolefins which may also be used are those produced by cracking of high molecular weight olefinic polymers or copolymers into compounds with a molecular weight within the range of molecular weights defined above.

Polypropylenes with an average molecular weight of about 750 to 100, for example about 800, polyisobutenes with an average molecular weight of about 1000 to 1500, for example 1300, are non limiting examples of specific compounds which are preferably used.

In a further preferred embodiment of the invention, constituent (L) is a mixture comprising a major proportion of polyisobutene-ethylenediamine and a minor proportion of polyisobutene. This mixture is more preferably dissolved in a hydrocarbon solvent to facilitate incorporation into the fuel. The proportion of aminated polymer in the mixture is normally about 50% to about 80% by weight, for example about 60% by weight and the proportion of hydrocarbon polymer is normally about 5% to about 30% by weight, preferably about 10% to about 25% by weight.

The polyisobutene-ethylenediamine compound has the following general formula:

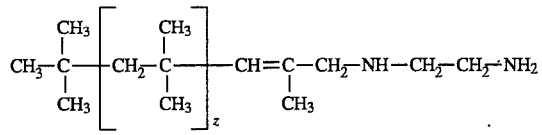

where z is a number from about 10 to about 40, preferably about 30 to about 35, for example about 33.

The polyisobutene compound has the following general formula:

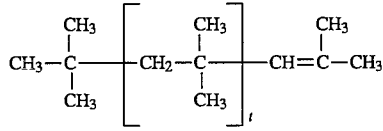

where t is a number from about 10 to about 40, preferably about 30 to about 35, for example about 33.

The solvent employed to dissolve the polymeric compounds and facilitate their incorporation into the fuel is more preferably a light aromatic distillate. Constituent (L) may comprise a polyisobutene and a polyisobutene-ethylenediamine as described above, dissolved in a light aromatic distillate, as sold under the trade name ORONITE OGA-472 by CHEVRON CHEMICAL COMPANY. ORONITE OGA-472 is a composition comprising approximately 60% by weight of polyisobutene-ethylenediamine, approximately 27% by weight of polyisobutene and approximately 13% by weight of light aromatic distillate comprising xylene and $C_9$ alkylbenzenes.

Formulations in accordance with the present invention also contain at least one constituent (M) selected from the group formed by mineral or synthetic lubricating oils and polyglycols which are soluble in said fuel, preferably having an average molecular weight of 480 to 2100 and with general formula (VIII):

$$HO-R(-O-R)_{\overline{x}}O-R-OH \qquad (VIII)$$

where each group R independently represents a hydrocarbon group containing 2 to 6 carbon atoms and x represents the average degree of polymerisation. These polyglycols are, for example, described in our European patent application EP-A-349 369.

Constituent (M) is advantageously a polyglycol having a polydispersity index of about 1 to about 1.25, preferably about 1 to about 1.15, with general formula (VIII) where each group R independently represents a linear or branched alkylene group containing 2 to 4 carbon atoms, preferably an ethylene or propylene group.

Particularly preferred polyglycols with formula (VIII) are those in which each group R represents a propylene group with formula:

$$CH_3-\underset{|}{CH}-CH_2-$$

The polyglycol is preferably a polyglycol with an average molecular weight of 600 to 1800, more preferably 650 to 1250.

Non limiting examples of mineral or synthetic lubricating oils which may be used as constituent (M) are mineral oils such as lubricating oils known in the art under the denominations 500 NS and 600 NS, and synthetic lubricating oils such as polyol ethers and esters, in particular polyoxyalkyleneglycol ethers.

The formulations of the invention are particularly useful as additives exhibiting good anticorrosive properties in a fuel based on a hydrocarbon or a mixture of hydrocarbons and at least one oxygenated compound selected from the group formed by alcohols and ethers. These formulations are also useful as multifunctional additives exhibiting particularly good anti-ORI and detergent-dispersant properties for an engine fuel for a spark ignition engine, based on a hydrocarbon or a mixture of hydrocarbons and at least one oxygenated compound selected from the group formed by alcohols and ethers. These formulations are generally added to the fuel so as to produce a concentration by weight of additive composition in the engine fuel of 10 to 10000 ppm, preferably 100 to 5000 ppm and more preferably 100 to 2000 ppm.

Formulations in accordance with the present invention have a weight ratio of constituent (K) to constituent (L) [(K)/(L)] of generally about 0.02:1 to about 4:1.

This ratio is preferably about 0.02:1 to about 2:1 and more preferably about 0.1:1 to about 2:1.

The weight ratio of constituent (L) to constituent (M) [(L)/(M)] is generally about 0.05:1 to about 10:1. This ratio is preferably about 0.05:1 and more preferably about 0.01:1 to about 2:1.

The invention also relates to the alkoxylated heterocyclic imidazo-oxazole type compounds themselves having the formula (I) as described hereinabove.

The following examples illustrate the invention without limiting its scope.

EXAMPLE 1

106 grams (g) (0.5 mole) of 1-(2-hydroxyethyl)-2-heptyl-imidazoline and 10.8 g (0.16 mole) of sodium methylate were introduced into a 1 liter reactor equipped with a mechanical stirring system, a temperature measurement and regulation system and an acetone-dry ice cooled condenser. The mixture was brought to 120° C. with stirring and held for 1 hour under a vacuum of 10 mm of mercury. After being brought back to atmospheric pressure, 493 g (8.5 moles) of propylene oxide was slowly added over a period of 8 hours 30 minutes. The reaction medium was held at 120° C. for the entire addition period and then for a further 30 minutes following addition before cooling to a room temperature of about 20° C.

The product obtained was transferred to an Erlenmeyer flask fitted with a coolant then diluted with 300 ml of toluene. After addition of 89 g of Ambosol 500 resin (trade name of an acidic magnesium silicate sold by HOECHST), the medium was brought to a temperature of 75° C. for 1 hour with stirring. After filtration and evaporation of the solvent, 563 g (ie, 93% conversion) of the final desired product was obtained. The kinematic viscosity of the product, measured at 40° C., was 168 centistokes (cSt). The product was analysed using infrared spectrometry, mass spectrometry and elemental analysis. No intense band was observed at 1550–1600 cm$^{-1}$ in the infrared, the characteristic peak of the carbon-nitrogen double bond of the imidazoline ring. This product, with general formula (I) where R$^1$ represents a heptyl group with empirical formula —C$_7$H$_{15}$, R$^2$ represents a methyl group, A represents a 1-methyl dimethylene group, m and p equal zero and n equals 16, had a calculated molecular weight of 1199.7. Calculated and measured elemental analysis was as follows:

| Element | % measured | % calculated |
|---------|------------|--------------|
| H | 11.1 | 10.59 |
| C | 62.05 | 63.07 |
| N | 2.12 | 2.34 |
| O | | 24.01 |

The mass spectrum shown in FIG. 1 was obtained by electron impact in a magnetic sector apparatus using a 70 electron volt electron beam. It shows a fragment with molecular weight 59 of formula:

$$CH_2-\underset{|}{CH}-OH$$
$$CH_3$$

a fragment with molecular weight 117 and a fragment with molecular weight 175 of formula:

$$\left( CH_2-\underset{\underset{CH_3}{|}}{CH}-O \right)_y CH_2-\underset{\underset{CH_3}{|}}{CH}-OH$$

where y is respectively 1 and 2, and a fragment with molecular weight 239 of formula:

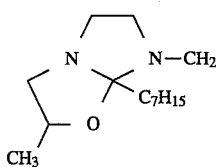

EXAMPLE 2

Detergent Composition 1018 g of polyisobutenylsuccinic anhydride (PIBSA) from the condensation of polyisobutene (polyisobutene with an average molecular weight of 920) with maleic anhydride (analysis of the anhydride functions in this product indicated a 0.7 anhydride function per kilogram) and 1018 g of xylene were placed in a 2 liter reactor equipped with a mechanical stirrer, a Dean-Stark separator and a temperature regulation system.

148 g (0.423 mole) of 1-(2-hydroxyethyl)-2-heptadecenyl imidazoline diluted in 148 g of xylene was then added dropwise at room temperature and with stirring. Addition was effected over a period of 30 minutes and accompanied by a rapid temperature increase in the reaction mixture of about 5° C. The mixture was then refluxed for 3 hours and the reaction water eliminated by azeotropic distillation. 2.3 ml (milliliters) of water was recovered. The progress of the reaction could also be followed by infrared spectrometry at the imine group absorption band of 1 660 cm$^{-1}$ which gradually disappeared during the course of the reaction.

The reactor temperature was reduced to 50° C. then maintained at that level during dropwise addition of 56 g (0.297 mole) of tetraethylenepentamine diluted in 49 g of xylene. Following addition, the mixture was again refluxed for 15 minutes. Water was again eliminated. The total amount of water recovered in the two reaction steps was 7.2 ml. The infrared spectrum contained two absorption bands (1710 cm$^{-1}$ and 1770 cm$^{-1}$) which are characteristic of the succinamide group, with a shoulder (1740 cm$^{-1}$) which is characteristic of the ester group.

A solution in xylene was thus obtained containing 50% by weight of active ingredient, of a composition whose elemental analysis indicated a nitrogen content of 2.55% by weight.

EXAMPLE 3

Solutions of formulations F1 to F7 comprising various amounts by weight of constituent K, L and M as defined below, were prepared in xylene.

Constituent K consisted of the product obtained in example 1.

Constituent L consisted of the composition obtained in example 2.

Constituent M was a polypropyleneglycol with formula:

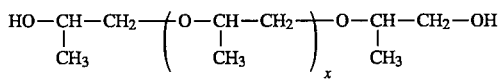

with an average molecular weight of 922 (x=13.6) and a polydispersity of 1.1.

Formulation F1 in accordance with the present invention contained constituent K obtained from example 1, constituent L and constituent M as described above. These constituents had a weight ratio K:L:M of 1:5:4 in terms of active ingredient.

Formulation F2 (comparative formulation, contained constituent L and constituent M as described above, but no constituent K. The active ingredient weight ratio L:M was 1.25:1.

Formulation F3 (comparative formulation) contained constituent L as described above, but no constituent K or M.

Formulation F4 (comparative formulation) contained constituent M as described above, but no constituent K or L.

Formulation F5 (comparative formulation) contained constituent K and constituent L as described above, but no constituent M. The active ingredient weight ratio K:L was 0.2:1.

Formulation F6 (comparative formulation) contained constituent K and constituent M as described above, but no constituent L. The active ingredient weight ratio K:M was 0.25:1.

Formulation F7 (comparative formulation) contained constituent K as described above, but no constituent L or M.

EXAMPLE 4

A series of, tests was carried out to evaluate the octane requirement increase limitation properties of an engine supplied with pure fuel and with a fuel containing one of the formulations described in example 3.

Fuel (S1) was a lead free fuel comprising, by volume:

16% aromatics

14% olefins 59.6% saturated compounds (paraffins and naphthenes)

10.4% methyltertiobutylether.

The different formulations were added to the fuel in a concentration by weight of active ingredient of 600 ppm.

The tests were conducted on an engine test bed equipped with a Renault type F3N engine with a cylinder capacity of 1721 cm$^3$ and a compression ratio of 9.5. The tests were conducted following the Renault 22 700 procedure, at a cylinder head water temperature of 95° C. plus or minus 2 degrees and an oil manifold temperature of 140° C. The test cycle took 12 hours (h) and comprised:

1 h idling at no load 4 h at 2500 revolutions per minute (rpm) at half load 3 h at 3 500 rpm on no load 4 h at 2 500 rpm at half load.

Spark advance values corresponding to the onset of pinking, expressed in crankshaft degrees and designated by the initials KLSA (Knock Limit Spark Advance) were determined at 0, 50, 100, 150, 200, 300 and 400 hours for 7 different operating conditions of the engine: 1500, 2000, 2500, 3000, 3500, 4000 and 4500 rpm. The results obtained were expressed in terms of the variations in knock limit spark advance between 0 and 400 hours (ΔKLSA) at the different operating regimes of the engine and are shown in Table II below. The average weight of deposits formed on the intake valves (expressed in milligrams (mg) per valve) are also shown in Table II.

These results show that the fuel containing the formulation of the invention produced lower ΔKLSA values than the pure fuel or the comparative fuels containing the majority of formulations and thus limits the engine octane requirement increase and retards the onset of pinking. It can also be seen that the formulation, of the invention reduces the weight of deposits on the intake valves compared to that obtained using the pure fuel or with the comparative fuels containing the majority of formulations.

In addition, it can be seen that the fuel containing formulation F7 was effective in limiting the engine octane requirement increase but is not effective in limiting the weight of deposits formed on the intake valves.

TABLE II

| ΔKLSA (°V) at 400 h Engine operation | *pure fuel (S1) | S1 +F1 | *S1 +F2 | *S1 +F3 | *S1 +F4 | *S1 +F5 | *S1 +F6 | *S1 +F7 |
|---|---|---|---|---|---|---|---|---|
| 1500 rpm | 8 | 5 | 8 | 9 | 8 | 7 | 7 | 6 |
| 2000 rpm | 10 | 6 | 9 | 10 | 9 | 8 | 8 | 7 |
| 2500 rpm | 12 | 9 | 11 | 13 | 11 | 10 | 9 | 9 |
| 3000 rpm | 13 | 8 | 13 | 13 | 13 | 9 | 11 | 9 |
| 3500 rpm | 11 | 5 | 11 | 12 | 10 | 7 | 8 | 6 |
| 4000 rpm | 9 | 4 | 8 | 10 | 8 | 6 | 7 | 5 |
| 4500 rpm | 7 | 5 | 7 | 8 | 7 | 7 | 6 | 4 |
| Valve deposits mg/valve | 103 | 8 | 8 | 15 | 110 | 76 | 92 | 149 |

*Comparative

EXAMPLE 5

The carburettor cleaning properties of fuels containing the formulations prepared in example 3 were evaluated, The engine test procedure was conducted following European standard R5-CEC-F03-T-81, The results were expressed in terms of a value of zero to ten, A value of 10 corresponded to a clean carburettor and a value of 0 corresponded to a very coked carburettor. The formulations were added to a fuel in concentrations by weight of active ingredient in the fuel shown for each example in Table III below:

TABLE III

| FUEL ADDITIVE | QUANTITY OF ADDITIVE | VALUE |
|---|---|---|
| *pure fuel | 0 ppm | 3.31 |
| fuel + formulation F1 | 600 ppm | 9.25 |
| *fuel + formulation F2 | 600 ppm | 9.18 |
| *fuel + formulation F3 | 600 ppm | 9.12 |
| *fuel + formulation F4 | 600 ppm | 3.82 |
| *fuel + formulation F5 | 600 ppm | 9.15 |
| *fuel + formulation F6 | 600 ppm | 9.01 |
| *fuel + formulation F7 | 600 ppm | 9.07 |

*Comparative

The fuel used in these tests was a supergrade lead free petrol (S2) with an engine octane number of 85.8 and a research octane number of 96.4. The supergrade petrol had an initial distillation point of 35° C. and a final distillation point of 204° C.

The composition by volume of the supergrade petrol was:
55.6% saturated compounds (paraffins+ naphthenes)
10.8% olefins
33.6% aromatics.

EXAMPLE 6

A series of tests was conducted to evaluate the valve cleaning properties of various formulations. The tests were conducted on a Mercedes M102E engine test bed without additives and with addition of additives to the fuel. The test procedure was a conventional procedure comprising the use of a 4 cylinder engine, type Mercedes M102 E, with a cylinder capacity of 2299 $cm^3$ and a compression ratio of 9/1. The test procedure was cyclic, each cycle comprising four successive operating periods:

30 s (seconds) at 800 rpm (revolutions per minute) at zero load, 60 s at 1300 rpm at a load of 31 newtons (m×kg×$s^{-2}$), 120 s at 1850 rpm at a load of 34 newtons and 60 s at 3000 rpm at a load of 37 newtons.

Each test period was normally 60 hours. At the start of each test, the engine was fitted with new, weighed valves. At the end of the test, the valves were removed, washed with hexane, dried, then weighed after physical elimination (by scratching) of the deposits formed on the combustion chamber side of the valve. The results shown below are average values for the weight of deposit on a valve, calculated from the amount of deposit measured on the annular contact of each intake valve, by taking the difference between the weight of the new valve and the weight of said valve at the end of each test after elimination of the deposits on the combustion chamber side. A visual estimation was also made of the state of each valve (intake, annular contact side) by assigning a value between 1 and 10 in accordance with the procedure known as the CRC (Coordinating Research Council) procedure; the results expressed below are an average value per valve; a value of 10 corresponds to a clean valve and a value of 1 to a very coked valve.

The fuel used for these tests was the lead free supergrade petrol with the characteristics given in example 5 above.

The formulations were added to the fuel in quantities sufficient to produce the concentrations of active ingredient indicated for each example in Table IV:

TABLE IV

| Fuel | Amount of additive | Average deposit, mg | Average CRC |
|---|---|---|---|
| *Pure fuel (S2) | 0 ppm | 337 | 8.11 |
| S2 + F1 | 600 ppm | 42 | 9.44 |
| *S2 + F2 | 600 ppm | 48 | 9.40 |
| *S2 + F3 | 600 ppm | 121 | 8.53 |
| *S2 + F4 | 600 ppm | 343 | 8.05 |
| *S2 + F5 | 600 ppm | 152 | 8.47 |
| *S2 + F6 | 600 ppm | 171 | 8.32 |
| *S2 + F7 | 600 ppm | 329 | 8.10 |

*Comparative

EXAMPLE 7

Anticorrosive tests were conducted on the formulations prepared in example 3. The tests consisted of determining the extent of corrosion produced on samples of basic polished steel, in the presence of water, using modified standard ASTM D 665 (temperature 32.2° C., duration 20 hours). The results were expressed as percentage (%) of the sample surface which had corroded after 20 hours. The fuel used was a Diesel fuel having the following principal characteristics:

| Limiting filtering temperature | 4° C. |
|---|---|
| Initial distillation point | 160° C. |
| 95% distillation point | 370° C. |
| Density at 15° C. | 0.84 |
| Calculated cetane number | 52 |

The formulation was added to the fuel to produce the concentrations of active ingredient which are shown in Table V below:

TABLE V

| FUEL ADDITIVE | AMOUNT OF ADDITIVE | % OF SURFACE CORRODED |
|---|---|---|
| *Pure fuel | 0 ppm | 100 |
| Fuel + formulation F1 | 600 ppm | 0 |
| *Fuel + formulation F2 | 600 ppm | 0 |
| *Fuel + formulation F3 | 600 ppm | 0 |
| *Fuel + formulation F4 | 600 ppm | 100 |
| *Fuel + formulation F5 | 600 ppm | 50 |
| *Fuel + formulation F6 | 600 ppm | 100 |
| *Fuel + formulation F7 | 600 ppm | 100 |

*Comparative

Analysis of the results obtained in the previous examples shows that formulations in accordance with the present invention significantly limit octane requirement increase in spark ignition engines and also have both intake system detergent properties and anticorrosive properties.

The entire disclosure of all applications, patents, and publications cited herein and of corresponding French Application 93 06688, filed Jun. 2, 1993, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A fuel additive comprising at least one constituent (K), at least one constituent (L) and at least one constituent (M), said constituent (K) being at least one heterocyclic imidazooxazole compound containing an alkoxylated side chain and having general formula (I):

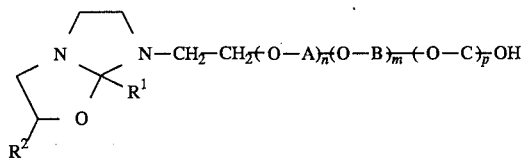

where $R^1$ represents a hydrogen atom or a hydrocarbon group containing 1 to 40 carbon atoms, $R^2$ represents a hydrogen atom or a hydrocarbon group containing 1 to 12 carbon atoms, A, B, and C, which may be identical or different, each represent a divalent hydrocarbon group containing 2 to 6 carbon atoms, n is a whole number from 5 to 50, said constituent (L) being of at least one compound selected from the group consisting of detergent-dispersant products, and said constituent (M) being at least one compound selected from the group consisting of mineral and synthetic lubricating oils and polyglycols which are soluble in said fuel.

2. A fuel additive according to claim 1 where constituent (K) is selected from compounds with general formula (I) where $R^1$ represents a hydrogen atom or a hydrocarbon group containing 4 to 25 carbon atoms, $R^2$ represents a hydrogen atom or a hydrocarbon group containing 1 to 6 carbon atoms, A, B and C, which may be identical or different, each represent a divalent hydrocarbon group containing 2 to 4 carbon atoms, n is a whole number from 10 to 50, m and p, which may be identical or different, are each zero or a whole number from 1 to 25, and the sum n+m+p is a whole number from 10 to 50.

3. A fuel additive according to claim 1, wherein constituent (K) is selected from compounds with general formula (I) where $R^1$ represents a hydrogen atom or a hydrocarbon group containing 4 to 25 carbon atoms, $R^2$ represents a hydrogen atom or a hydrocarbon group containing 1 to 3 carbon atoms, A, B and C, which may be identical or different, each represent a divalent hydrocarbon group containing 2 to 4 carbon atoms, n is a whole number from 10 to 25, m and p, which may be identical or different, are each zero or a whole number from 1 to 25, and the sum n+m+p is a whole number from 10 to 25.

4. A fuel additive according to claim 1 wherein constituent (K) is selected from compounds with general formula (I) where $R^1$ represents a hydrogen atom or an alkoyl, alkenyl, aryl, alkaryl or aralkyl group, $R^2$ represents a hydrogen atom or a linear or branched, alkoyl group, m and p equal zero and A represents a dimethylene, 1-methyl dimethylene or 1-ethyl dimethylene group.

5. A fuel additive according to claim 1 wherein constituent (K) is selected from compounds with general formula (I) where $R^1$ represents a hydrogen atom or a linear or branched alkoyl or alkenyl group.

6. A fuel additive according to claim 1 wherein constituent (L) is selected from the group consisting of polyolefins, polyisobutene-amines, and mixtures of these compounds, the products resulting from reaction in a first step of at least one succinic derivative selected from the group consisting of alkenylsuccinic acids and anhydrides and polyalkenylsuccinic acids and anhydrides and polyalkenyisuccinic acids and anhydrides, with at least one 1-(2-hydroxyethyl)-imidazoline substituted in the 2 position by a linear or branched alkyl or alkenyl radical containing 1 to 25 carbon atoms, the imidazoline/succinic derivative molar ratio being from 0.1:1 to 0.9:1, said step being carried out under conditions such that at least 0.15 moles of water per mole of imidazoline used is formed and eliminated; and in a second step of the reaction, the product from the first step is reacted with at least one polyamine having one of the following general formulae:

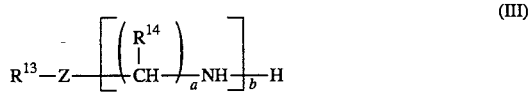

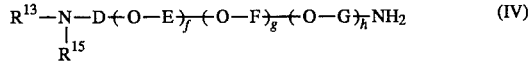

where $R^{13}$ represents a hydrogen atom or a hydrocarbon group containing 1 to 60 carbon atoms, Z is —O— or —$NR^{15}$—, where $R^{15}$ represents a hydrogen atom or a hydrocarbon group containing 1 to 60 carbon atoms, $R^{13}$ and $R^{15}$ being capable of forming a heterocycle with the nitrogen atom to which they are bonded, each $R^{14}$ group independently represents a hydrogen atom or a hydrocarbon group containing 1 to 4 carbon atoms, a is a whole number from 2 to 6, b is a whole number from 1 to 10 when Z is —$NR^{15}$— and a whole number from 2 to 10 when Z is —O—; D, E, F and G, which may be identical or different, each represent a divalent hydrocarbon group containing 2 to 6 carbon atoms, f is a whole number from 1 to 60, g and h, which may be identical or different, are each zero or a whole number from 1 to 50 and the sum f+g+h is a whole number from 1 to 60, the quantity of polyamine used in the reaction being at least 0.1 mole per mole of succinic derivative introduced in the first step.

7. A fuel additive according to claim 1 wherein constituent (L) comprises a product resulting from a reaction in a first step between at least one succinic derivative selected from the group consisting of alkenylsuccinic and polyalkenylsuccinic anhydrides having an average molecular weight of 200 to 3000, and at least one 1-(2-hydroxyethyl)-imidazoline substituted in the 2 position selected from the group consisting of 1-(2-hydroxyethyl)-2-2-heptadecenylimidazoline and 1-(2-hydroxyethyl)-2-methylimidazoline; and in a second step of the reaction, the product from the first step is reacted with at least one polyamine having one of the following general formulae:

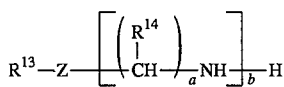 (III)

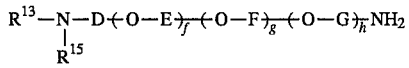 (IV)

wherein Z represents a $-NR^{15}-$ group, $R^{13}$, $R^{14}$ and $R^{15}$ each represent a hydrogen atom, a equals 2 and b is a whole number from 1 to 5, D, E, F and G, which may be identical or different, each represent an alkylene group containing 2 to 3 carbon atoms, f is a whole number from 1 to 60 and g and h equal zero or f is a whole number from 1 to 59, h is zero or a whole number such that the sum f+h is from 1 to 59 and g is a whole number from 1 to 50, and in each case the sum f+g+h is a whole number from 1 to 60.

8. A fuel additive according to claim 1, wherein constituent (L) is selected from the group consisting of polyisobutenes, polyisobutene-amines and mixtures of these compounds.

9. A fuel additive according to claim 1 wherein constituent (M) is selected from the group consisting of mineral and synthetic lubricating oils, and polyglycols which are soluble in said fuel and are of the general formula (VIII):

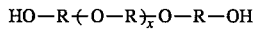 (VIII)

wherein each group R independently represent a hydrocarbon group containing 2 to 6 carbon atoms and x represents the average degree of polymerization.

10. A fuel additive according to claim 9 wherein constituent (M) is a polyglycol having a polydispersity index of about 1 to about 125, of the general formula (VIII) where each R group independently represents a linear or branched alkylene group containing 2 to 4 carbon atoms.

11. A fuel additive according to claim 9 wherein constituent (M) is a polyglycol of the general formula (VIII) wherein each E group independently represents a propylene group of the formula:

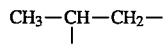

having an average molecular weight of 600 to 1800.

12. A fuel additive comprising a formulation according to claim 1 and at least one oxygenated compound selected from the group formed by alcohols and ethers.

13. A fuel composition comprising a hydrocarbon fuel suitable for spark ignition engines and a fuel additive according to claim 12.

14. A fuel composition according to claim 13 wherein 10 to 10000 ppm by weight of the fuel additive is added to the fuel.

15. A fuel composition according to claim 14 wherein the fuel additive comprises constituents (K), (L) and (M) in a weight ratio [(K)/(L)] of about 0.02:1 to about 4:1 and [(L)/(M)] of about 0.05:1 to about 10:1.

16. A heterocyclic imidazo-oxazole type compound containing an alkoxylated side chain and having general formula (I):

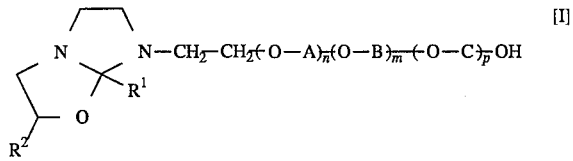 [I]

where $R^1$ represents a hydrogen atom or a hydrocarbon group containing 1 to 40 carbon atoms, $R^2$ represents a hydrogen atom or a hydrocarbon group containing 1 to 12 carbon atoms, A, B, and C, which may be identical or different, each represent a divalent hydrocarbon group containing 2 to 6 carbon atoms, n is a whole number from 5 to 50, m and p, which may be identical or different, are each zero or a whole number from 1 to 25, and the sum n+m+p is a whole number from 5 to 50.

17. A compound according to claim 16 with general formula (I) where $R^1$ represents a hydrogen atom or a hydrocarbon group containing 4 to 25 carbon atoms, $R^2$ represents a hydrogen atom or a hydrocarbon group containing 1 to 6 carbon atoms, A, B, and C, which may be identical or different, each represent a divalent hydrocarbon group containing 2 to 4 carbon atoms, n is a whole number from 10 to 50, m and p, which may be identical or different, are each zero or a whole number from 1 to 25, and the sum n+m+p is a whole number from 10 to 50.

18. A compound according to claim 16 with general formula (I) where $R^1$ represents a hydrogen atom or a hydrocarbon group containing 4 to 25 carbon atoms, $R^2$ represents a hydrogen atom or a hydrocarbon group containing 1 to 3 carbon atoms, A, B, and C, which may be identical or different, each represent a divalent hydrocarbon group containing 2 to 4 carbon atoms, n is a whole number from 10 to 25, m and p, which may be identical or different, are each zero or a whole number from 1 to 25, and the sum n+m+p is a whole number from 10 to 25.

19. A compound according to claim 16 with general formula (I) where $R^1$ represents a hydrogen atom or an alkoyl, alkenyl, aryl, alkaryl or aralkyl group, $R^2$ represents a hydrogen atom or a linear or branched, alkoyl group, m and p equal zero and A represents a dimethylene, 1-methyl dimethylene or 1-ethyl dimethylene group.

20. A compound according to claim 16 with general formula (I) where $R^1$ represents a hydrogen atom or a linear or branched alkoyl or alkenyl group.

21. A fuel additive according to claim 8, wherein constituent (L) is a mixture containing a minor proportion of polyisobutenes and a major proportion of polyisobutene-ethylenediamines.

22. A fuel additive according to claim 9, wherein constituent (M) has an average molecular weight of 480 to 2100.

23. A fuel additive according to claim 10, wherein the R group is an ethylene or propylene group.

24. A fuel additive according to claim 11, wherein constituent (M) has an average molecular weight to 600 to 1800.

* * * * *